United States Patent
Nair et al.

(10) Patent No.: US 9,656,934 B2
(45) Date of Patent: *May 23, 2017

(54) PROCESS FOR PRODUCING PHENOL AND/OR CYCLOHEXANONE

(71) Applicant: ExxonMobil Chemical Patents Inc., Baytown, TX (US)

(72) Inventors: Hari Nair, Somerville, NJ (US); Christopher L. Becker, Manhattan, KS (US); Karen S. Nimmo, Dickinson, TX (US); James R. Lattner, LaPorte, TX (US); Francisco M. Benitez, Cypress, TX (US); Charles Morris Smith, Princeton, NJ (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/892,513

(22) PCT Filed: Jun. 6, 2014

(86) PCT No.: PCT/US2014/041402
§ 371 (c)(1),
(2) Date: Nov. 19, 2015

(87) PCT Pub. No.: WO2014/209577
PCT Pub. Date: Dec. 31, 2014

(65) Prior Publication Data
US 2016/0102034 A1 Apr. 14, 2016

Related U.S. Application Data

(60) Provisional application No. 61/841,060, filed on Jun. 28, 2013.

(30) Foreign Application Priority Data

Sep. 11, 2013 (EP) .................................... 13183955

(51) Int. Cl.
*C07C 45/53* (2006.01)
*C07C 37/08* (2006.01)
*C07C 2/74* (2006.01)
*C07C 407/00* (2006.01)

(52) U.S. Cl.
CPC ................ *C07C 37/08* (2013.01); *C07C 2/74* (2013.01); *C07C 45/53* (2013.01); *C07C 407/00* (2013.01); *C07C 2101/14* (2013.01)

(58) Field of Classification Search
CPC ............ C07C 45/53; C07C 37/08; C07C 2/74
USPC ................................. 568/342, 798; 585/467
See application file for complete search history.

(56) References Cited

U.S. PATENT DOCUMENTS

| 4,490,565 A | 12/1984 | Chang et al. |
| 5,254,751 A | 10/1993 | Zakoshansky |
| 6,037,513 A | 3/2000 | Chang et al. |

FOREIGN PATENT DOCUMENTS

| WO | 00/14042 | 3/2000 |
| WO | 2004/009522 | 1/2004 |
| WO | 2012/067711 | 5/2012 |
| WO | 2012/145031 | 10/2012 |
| WO | 2012/145032 | 10/2012 |

OTHER PUBLICATIONS

Koltunov et al., "Efficient Cleavage of Cumene Hydroperoxide over HUSY zeolites: The role of Bronsted activity", Applied Catalysis A: General, 336 (2008), pp. 29-34.

*Primary Examiner* — Sikarl Witherspoon

(57) ABSTRACT

In a process for producing phenol, a cleavage feed comprising cyclohexylbenzene hydroperoxide is supplied to a cleavage reaction zone and a cleavage reaction mixture comprising the cleavage feed is contacted in the cleavage reaction zone with a solid acid catalyst under conditions effective to produce a cleavage effluent comprising phenol and cyclohexanone. The cleavage effluent is then divided into at least a cleavage product and a cleavage recycle and the cleavage recycle and a polar solvent is supplied to the cleavage reaction zone to produce the cleavage reaction mixture with the cleavage feed. Preferably, the polar solvent is combined with the cleavage recycle before being charged into the cleavage reaction zone.

22 Claims, 1 Drawing Sheet

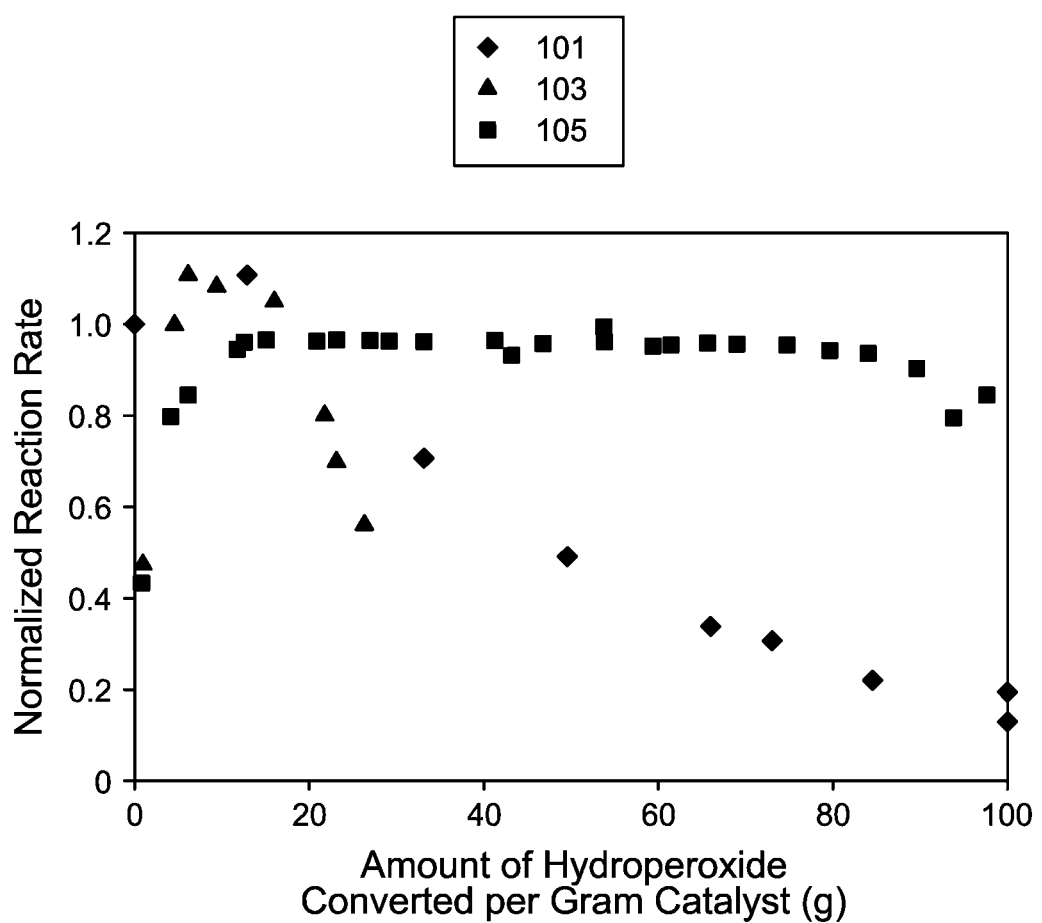

PROCESS FOR PRODUCING PHENOL AND/OR CYCLOHEXANONE

PRIORITY CLAIM

This application claims priority to U.S. Provisional Application Ser. No. 61/841,060 filed Jun. 28, 2013, and European Application No. 13183955.7 filed Sep. 11, 2013, the disclosures of which are fully incorporated herein by their reference.

FIELD

The present disclosure relates to a process for producing phenol and/or cyclohexanone.

BACKGROUND

Phenol and cyclohexanone are important products in the chemical industry and are useful in, for example, the production of phenolic resins, bisphenol A, ε-caprolactam, adipic acid, and plasticizers.

Currently, a common route for the production of phenol is the three-step Hock process via cumene. In the first step of the process benzene is alkylated with propylene in the presence of an acidic catalyst to produce cumene. The second step comprises oxidation, preferably aerobic oxidation, of cumene to the corresponding cumene hydroperoxide. The third step comprises cleavage of the cumene hydroperoxide, usually in the presence of a sulfuric acid catalyst, into substantially equimolar amounts of phenol and acetone, a co-product.

It is known that phenol and cyclohexanone can be co-produced from cyclohexylbenzene in which cyclohexylbenzene is oxidized to obtain cyclohexylbenzene hydroperoxide and the hydroperoxide is decomposed in the presence of an acid catalyst to the desired phenol and cyclohexanone. Although various methods are available for the production of cyclohexylbenzene, a preferred route is provided in U.S. Pat. No. 6,037,513, which discloses that cyclohexylbenzene can be produced by contacting benzene with hydrogen in the presence of a bifunctional catalyst comprising a molecular sieve of the MCM-22 family and at least one hydrogenation metal selected from palladium, ruthenium, nickel, cobalt and mixtures thereof. This patent reference also discloses that the resultant cyclohexylbenzene can be oxidized to the corresponding hydroperoxide which is then decomposed to the desired phenol and cyclohexanone co-product.

In the cumene-based Hock process, reaction product effluent from the cumene oxidation step is first concentrated to greater than 80 wt % by removing unreacted cumene under vacuum, and the resultant concentrate is then sent to the cleavage reactor. In addition to the hazards associated with handling concentrated hydroperoxide, the cleavage poses safety concerns due to the rapid and highly exothermic nature of the reaction. Further, significant amounts of by-products may be generated from the concentrated oxidation products. In practice, therefore, the concentrated cumene hydroperoxide is often diluted with solvents, such as acetone, in order to better manage the heat of reaction and to control by-product formation. For example, U.S. Pat. No. 5,254,751 discloses a method of producing phenol and acetone by decomposing cumene hydroperoxide in a non-isothermal manner in the presence of excess acetone whereby the molar ratio of acetone to phenol in a decomposition reactor is from about 1.1:1 to 1.5:1.

The process for making phenol from cyclohexylbenzene differs from the cumene process in several respects. Firstly, oxidation of cyclohexylbenzene to cyclohexylbenzene hydroperoxide is much more difficult than oxidation of cumene and requires elevated temperatures and the use of a catalyst, such as N-hydroxyphthalimide (NHPI). As a result, the cyclohexylbenzene oxidation effluent is also generally at elevated temperatures so that cooling this stream back to ambient temperature would incur additional operating cost. Also, in view of the high boiling point of cyclohexylbenzene, concentration of the cyclohexylbenzene hydroperoxide by evaporation of the residual cyclohexylbenzene is much more difficult. In addition, the cleavage chemistry for cyclohexylbenzene hydroperoxide is much more complicated than that for cumene hydroperoxide, particularly since more routes for by-product formation exist with cyclohexylbenzene hydroperoxide cleavage. Moreover, cyclohexanone is much more prone to acid-catalyzed aldol condensation reactions than acetone so that significant yield loss is possible unless the cyclohexylbenzene hydroperoxide cleavage is closely controlled.

There are other disadvantages of using sulfuric acid for cyclohexylbenzene hydroperoxide cleavage: 1) sulfuric acid is corrosive, especially in the presence of water, requiring expensive materials for reactor construction; 2) sulfuric acid needs to be neutralized before product separation and distillation, which requires additional chemicals such as phenate, caustics, or organic amines; and 3) the salt generated from neutralization requires separation and disposal and the waste water needs to be treated. Therefore, there are strong incentives to replace sulfuric acid with a heterogeneous cleavage catalyst that eliminates these drawbacks.

U.S. Pat. No. 4,490,565 discloses that zeolite beta can be an effective replacement for sulfuric acid in the cleavage of cumene hydroperoxide and that the yields, conversions and selectivities are generally superior to those produced by the use of the large pore zeolites X and Y. In U.S. Pat. No. 4,490,566, similar improvements over the large pore zeolites X and Y are reported with intermediate pore size zeolites, such as ZSM-5. In contrast, in an article entitled "Efficient Cleavage of Cumene Hydroperoxide over HUSY zeolites: The role of Bronsted activity", *Applied Catalysis A: General*, 336 (2008), pages 29-34, Koltonov et al. report that cumene hydroperoxide readily undergoes decomposition over HUSY zeolites of high (15 to 40) Si/Al ratio with good selectivity to phenol and acetone and with efficiency even comparable to that of sulfuric acid. Despite or possibly because of these varying recommendations, most commercial processes for the cleavage of cumene hydroperoxide continue to use sulfuric acid as the catalyst.

In addition, International Patent Publication No. WO2012/145031 discloses that large pore zeolites of the FAU type having a unit cell size of less than 24.50 Å exhibit a unique combination of high activity and high selectivity activity for the conversion of cyclohexylbenzene hydroperoxide into phenol and cyclohexanone.

SUMMARY

Although a number of solid acids have shown promise as catalysts for the cleavage of cyclohexylbenzene hydroperoxide, to date their utility has been limited because of their tendency to undergo rapid deactivation. According to the present invention, it has now been found that the cycle life of solid acid catalysts used in the cleavage of conversion of cyclohexylbenzene hydroperoxide into phenol and cyclohexanone can be increased if part of the cleavage effluent is recycled to cleavage reaction and a polar solvent, especially water, is added to the cleavage effluent recycle.

In one aspect, the present disclosure relates to a process for producing phenol, the process comprising:

(a) supplying a cleavage feed comprising cyclohexylbenzene hydroperoxide to a cleavage reaction zone;

(b) contacting a cleavage reaction mixture comprising the cleavage feed in the cleavage reaction zone with a solid acid catalyst under conditions effective to produce a cleavage effluent comprising phenol and cyclohexanone;

(c) dividing the cleavage effluent into at least a cleavage product and a cleavage recycle; and (d) supplying the cleavage recycle and a polar solvent to the cleavage reaction zone to produce the cleavage reaction mixture with the cleavage feed.

In a further aspect, the present disclosure relates to a process for producing phenol, the process comprising:

(a) hydroalkylating benzene with hydrogen in the presence of a hydroalkylation catalyst under conditions effective to produce a hydroalkylation reaction product comprising cyclohexylbenzene;

(b) contacting at least a portion of the cyclohexylbenzene from the hydroalkylation reaction product with oxygen in the presence of an oxidation catalyst under oxidation conditions effective to produce an oxidation product comprising cyclohexylbenzene hydroperoxide;

(c) supplying at least a portion of the oxidation product comprising cyclohexylbenzene hydroperoxide to a cleavage reaction zone;

(d) contacting a cleavage reaction mixture comprising the said oxidation product portion in the cleavage reaction zone with a solid acid catalyst under conditions effective to produce a cleavage effluent comprising phenol and cyclohexanone;

(e) dividing the cleavage effluent into at least a cleavage product and a cleavage recycle; and (f) supplying the cleavage recycle and a polar solvent to the cleavage reaction zone to produce the cleavage reaction mixture with said oxidation product portion.

BRIEF DESCRIPTION OF THE DRAWINGS

FIG. 1 is a graph of the normalized reaction rate (rate normalized to initial rate) as a function of the amount of cyclohexylbenzene hydroperoxide processed per gram of faujasite catalyst for the cyclohexylbenzene hydroperoxide cleavage tests described in Tests A, B, and C in the Example.

DETAILED DESCRIPTION

Various specific embodiments, versions and examples of the invention will now be described, including preferred embodiments and definitions that are adopted herein for purposes of understanding the claimed invention. While the following detailed description gives specific preferred embodiments, those skilled in the art will appreciate that these embodiments are exemplary only, and that the invention may be practiced in other ways. For purposes of determining infringement, the scope of the invention will refer to any one or more of the appended claims, including their equivalents, and elements or limitations that are equivalent to those that are recited. Any reference to the "invention" may refer to one or more, but not necessarily all, of the inventions defined by the claims.

In the present disclosure, a process is described as comprising at least one "step." It should be understood that each step is an action or operation that may be carried out once or multiple times in the process, in a continuous or discontinuous fashion. Unless specified to the contrary or the context clearly indicates otherwise, each step in a process may be conducted sequentially in the order as they are listed, with or without overlapping with one or more other step, or in any other order, as the case may be. In addition, one or more or even all steps may be conducted simultaneously with regard to the same or different batch of material. For example, in a continuous process, while a first step in a process is being conducted with respect to a raw material just fed into the beginning of the process, a second step may be carried out simultaneously with respect to an intermediate material resulting from treating the raw materials fed into the process at an earlier time in the first step. Preferably, the steps are conducted in the order described.

Unless otherwise indicated, all numbers indicating quantities in the present disclosure are to be understood as being modified by the term "about" in all instances. It should also be understood that the precise numerical values used in the specification and claims constitute specific embodiments. Efforts have been made to ensure the accuracy of the data in the examples. However, it should be understood that any measured data inherently contain a certain level of error due to the limitation of the technique and equipment used for making the measurement.

As used herein, the indefinite article "a" or "an" shall mean "at least one" unless specified to the contrary or the context clearly indicates otherwise. Thus, embodiments using "a fractionation column" include embodiments where one, two or more fractionation columns are used, unless specified to the contrary or the context clearly indicates that only one fractionation column is used. Likewise, "a C12+ component" should be interpreted to include one, two or more C12+ components unless specified or indicated by the context to mean only one specific C12+ component.

As used herein, "wt %" means percentage by weight, "vol %" means percentage by volume, "mol %" means percentage by mole, "ppm" means parts per million, and "ppm wt" and "wppm" are used interchangeably to mean parts per million on a weight basis. All "ppm" as used herein are ppm by weight unless specified otherwise. All concentrations herein are expressed on the basis of the total amount of the composition in question. All ranges expressed herein should include both end points as two specific embodiments unless specified or indicated to the contrary.

As used herein, a polar solvent is a solvent other than cyclohexanone and phenol exhibiting a polarity. Non-limiting polar solvents include water, alcohols, ketones, sulfones, ethers, esters, and the like. Non-limiting, specific examples of polar solvents that may be used in the process of the present disclosure are: water, $CH_3OH$, $CH_3CH_2OH$, n-propanol, isopropanol, 1-butanol, 2-butanol, cyclohexanol, furan, hydrofuran, tetrahydrofuran, dimethylsulfoxide, acetonitrile, acetone, and butanone.

Nomenclature of elements and groups thereof used herein are pursuant to the Periodic Table used by the International Union of Pure and Applied Chemistry after 1988. An example of the Periodic Table is shown in the inner page of the front cover of Advanced Inorganic Chemistry, $6^{th}$ Edition, by F. Albert Cotton et al. (John Wiley & Sons, Inc., 1999).

Described herein is a process for producing phenol by cleavage of cyclohexylbenzene hydroperoxide in the presence of a solid acid catalyst, such as an acidic molecular sieve. The cleavage process converts at least part of the cyclohexylbenzene hydroperoxide to phenol and cyclohexanone. The effluent from the cleavage reactor is divided into at least a cleavage product, from which phenol and/or cyclohexanone can be recovered, and a cleavage recycle, which is returned to the cleavage reactor. It has now been found that by supplying a polar solvent, desirably water, to the cleavage reactor along with the cleavage recycle, the cycle life of solid acid catalyst can be improved.

Preferably, the present cleavage process forms part of an integrated process for producing phenol and cyclohexanone from benzene, in which benzene is converted to cyclohexylbenzene, which is then oxidized to cyclohexylbenzene hydroperoxide, which, in turn, is cleaved to produce phenol and cyclohexanone. The present process will therefore now be more particularly described with reference to this preferred example.

Production of the Cyclohexylbenzene

In the initial step of the integrated process starting from benzene, cyclohexylbenzene is produced by reacting the benzene with cyclohexene in the presence of a catalyst having an alkylation function and under conditions to promote the following Reaction-1:

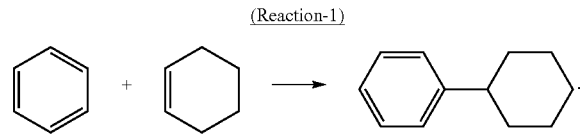 [SMILES: c1ccccc1 ; C1=CCCCC1 ; c1ccc(C2CCCCC2)cc1]

(Reaction-1)

The cyclohexene can be supplied to the reaction zone as a separate feed from the benzene, but normally is produced in situ by selective hydrogenation of the benzene in the presence of a hydrogenation component provided on the catalyst having the alkylation function. The bifunctional catalyst is therefore referred to herein as a hydroalkylation catalyst and overall the hydroalkylation reaction proceeds as follows to produce cyclohexylbenzene (CHB):

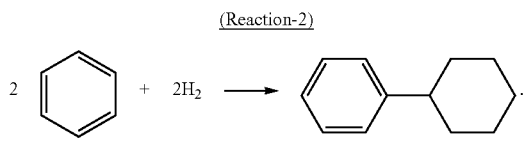

(Reaction-2)

U.S. Pat. Nos. 6,730,625 and 7,579,511, WO2009/131769, and WO2009/128984 disclose processes for producing cyclohexylbenzene by reacting benzene with hydrogen in the presence of a hydroalkylation catalyst, the contents of all of which are incorporated herein by reference in their entirety.

Any commercially available benzene feed can be used in the hydroalkylation step, but preferably the benzene has a purity level of at least 99 wt %. Similarly, although the source of hydrogen is not critical, it is generally desirable that the hydrogen is at least 99 wt % pure.

Conveniently, the total feed to the hydroalkylation step contains less than 1000 ppm, such as less than 500 ppm, for example less than 100 ppm, water. In addition, the total feed typically contains less than 100 ppm, such as less than 30 ppm, for example less than 3 ppm, sulfur and less than 10 ppm, such as less than 1 ppm, for example less than 0.1 ppm, nitrogen.

Hydrogen can be supplied to the hydroalkylation step over a wide range of values, but typically is arranged such that the molar ratio of hydrogen to benzene in the hydroalkylation feed is between about 0.15:1 and about 15:1, such as between about 0.4:1 and about 4:1, for example between about 0.4 and about 0.9:1.

In addition to the benzene and hydrogen, a diluent, which is substantially inert under hydroalkylation conditions, may be supplied to the hydroalkylation reaction. Typically the diluent is a hydrocarbon, in which the desired cycloalkylaromatic product, in this case cyclohexylbenzene, is soluble, such as a straight chain paraffinic hydrocarbon, a branched chain paraffinic hydrocarbon, and/or a cyclic paraffinic hydrocarbon. Examples of suitable diluents are decane and cyclohexane. Cyclohexane is a particularly attractive diluent since it is an unwanted by-product of the hydroalkylation reaction.

Although the amount of diluent is not narrowly defined, generally the diluent is added in an amount such that the weight ratio of the diluent to the aromatic compound is at least 1:100; for example at least 1:10, but no more than 10:1, typically no more than 4:1.

The hydroalkylation reaction can be conducted in a wide range of reactor configurations including fixed bed, slurry reactors, and/or catalytic distillation towers. In addition, the hydroalkylation reaction can be conducted in a single reaction zone or in a plurality of reaction zones, in which at least the hydrogen is introduced to the reaction in stages. Suitable reaction temperatures are between about 100° C. and about 400° C., such as between about 125° C. and about 250° C., while suitable reaction pressures are between about 100 kPa and about 7,000 kPa, such as between about 500 kPa and about 5,000 kPa.

The catalyst employed in the hydroalkylation reaction is a bifunctional catalyst comprising a molecular sieve of the MCM-22 family and a hydrogenation metal. The term "MCM-22 family material" (or "material of the MCM-22 family" or "molecular sieve of the MCM-22 family"), as used herein, includes one or more of:

molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference); ●molecular sieves made from a common second degree building block, being a 2-dimensional tiling of such MWW framework topology unit cells, forming a monolayer of one unit cell thickness, preferably one c-unit cell thickness;

molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and molecular sieves made by any regular or random 2-dimensional or 3-dimensional combination of unit cells having the MWW framework topology.

Molecular sieves of MCM-22 family generally have an X-ray diffraction pattern including d-spacing maxima at 12.4±0.25, 6.9±0.15, 3.57±0.07 and 3.42±0.07 Angstrom. The X-ray diffraction data used to characterize the material are obtained by standard techniques using the K-alpha doublet of copper as the incident radiation and a diffractometer equipped with a scintillation counter and associated computer as the collection system. Molecular sieves of MCM-22 family include MCM-22 (described in U.S. Pat. No. 4,954,325), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), MCM-36 (described in U.S. Pat. No. 5,250,277), MCM-49 (described in U.S. Pat. No. 5,236,575), and MCM-56 (described in U.S. Pat. No. 5,362,697). Other molecular sieves, such as UZM-8 (described in U.S. Pat. No. 6,756,030), may be used alone or in combination with MCM-22 family molecular sieves. Preferably, the molecular sieve is selected from (a) MCM-49; (b) MCM-56; and (c) isotypes of MCM-49 and MCM-56, such as ITQ-2.

Any known hydrogenation metal can be employed in the hydroalkylation catalyst, although suitable metals include palladium, ruthenium, nickel, zinc, tin, and cobalt, with palladium being particularly advantageous. Generally, the amount of hydrogenation metal present in the catalyst is between about 0.05 and about 10 wt %, such as between about 0.1 and about 5 wt %, of the catalyst. Where the MCM-22 family molecular sieve is an aluminosilicate, the amount of hydrogenation metal present can be such that the molar ratio of the aluminum in the molecular sieve to the hydrogenation metal is from about 1.5 to about 1500, for example from about 75 to about 750, such as from about 100 to about 300.

The hydrogenation metal may be directly supported on the MCM-22 family molecular sieve by, for example, impregnation or ion exchange. Preferably, at least 50 wt %, for example at least 75 wt %, and even substantially all of the hydrogenation metal is supported on an inorganic oxide separate from but composited with the molecular sieve. In particular, it is found that by supporting the hydrogenation metal on the inorganic oxide, the activity of the catalyst and its selectivity to cyclohexylbenzene and dicyclohexylbenzene are increased as compared with an equivalent catalyst in which the hydrogenation metal is supported on the molecular sieve.

The inorganic oxide employed in such a composite hydroalkylation catalyst is not narrowly defined provided it is stable and inert under the conditions of the hydroalkylation reaction. Suitable inorganic oxides include oxides of Groups 2, 4, 13, and 14 of the Periodic Table of Elements, such as alumina, titania, and/or zirconia. As used herein, the numbering scheme for the Periodic Table Groups is as disclosed in Chemical and Engineering News, 63(5), 27 (1985).

The hydrogenation metal is deposited on the inorganic oxide, conveniently by impregnation, before the metal-containing inorganic oxide is composited with the molecular sieve. Typically, the catalyst composite is produced by co-pelletization, in which a mixture of the molecular sieve and the metal-containing inorganic oxide are formed into pellets at high pressure (generally about 350 kPa to about 350,000 kPa), or by co-extrusion, in which a slurry of the molecular sieve and the metal-containing inorganic oxide, optionally together with a separate binder, are forced through a die. If necessary, additional hydrogenation metal can subsequently be deposited on the resultant catalyst composite.

Suitable binder materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be used as a binder include those of the montmorillonite and kaolin families, which families include the subbentonites and the kaolins commonly known as Dixie, McNamee, Ga. and Florida clays or others in which the main mineral constituent is halloysite, kaolinite, dickite, nacrite or anauxite. Such clays can be used in the raw state as originally mined or initially subjected to calcination, acid treatment or chemical modification. Suitable metal oxide binders include silica, alumina, zirconia, titania, silica-alumina, silica-magnesia, silica-zirconia, silica-thoria, silica-beryllia, silica-titania, as well as ternary compositions such as silica-alumina-thoria, silica-alumina-zirconia, silica-alumina-magnesia, and silica-magnesia-zirconia.

Although the hydroalkylation reaction using an MCM-22 family zeolite catalyst activated by the process described herein is highly selective towards cyclohexylbenzene, the effluent from the hydroalkylation reaction will inevitably contain some dicyclohexylbenzene by-product. Depending on the amount of this dicyclohexylbenzene, it may be desirable to either (a) transalkylate the dicyclohexylbenzene with additional benzene or (b) dealkylate the dicyclohexylbenzene to maximize the production of the desired mono-alkylated species.

Transalkylation with additional benzene is typically effected in a transalkylation reactor, separate from the hydroalkylation reactor, over a suitable transalkylation catalyst, such as a molecular sieve of the MCM-22 family, zeolite beta, MCM-68 (see U.S. Pat. No. 6,014,018), zeolite Y, and mordenite. The transalkylation reaction is typically conducted under at least partial liquid phase conditions, which suitably include a temperature of about 100 to about 300° C., a pressure of about 800 kPa to about 3500 kPa, a weight hourly space velocity of about 1 to about 10 $hr^{-1}$ on total feed, and a benzene/dicyclohexylbenzene weight ratio about of 1:1 to about 5:1.

Dealkylation or cracking is also typically effected in a reactor separate from the hydroalkylation reactor, such as a reactive distillation unit, at a temperature of about 150° C. to about 500° C. and a pressure of 15 psig to 500 psig (200 kPa to 3550 kPa) over an acid catalyst such as an aluminosilicate, an aluminophosphate, a silicoaluminphosphate, amorphous silica-alumina, an acidic clay, a mixed metal oxide, such as $WO_x/ZrO_2$, phosphoric acid, sulfated zirconia and mixtures thereof. Generally, the acid catalyst includes at least one aluminosilicate, aluminophosphate or silicoaluminphosphate of the FAU, AEL, AFI and MWW family. Unlike transalkylation, dealkylation can be conducted in the absence of added benzene, although it may be desirable to add benzene to the dealkylation reaction to reduce coke formation. In this case, the weight ratio of benzene to poly-alkylated aromatic compounds in the feed to the dealkylation reaction is typically from 0 to about 0.9, such as from about 0.01 to about 0.5. Similarly, although the dealkylation reaction can be conducted in the absence of added hydrogen, hydrogen is generally introduced into the dealkylation reactor to assist in coke reduction. Suitable hydrogen addition rates are such that the molar ratio of hydrogen to poly-alkylated aromatic compound in the total feed to the dealkylation reactor is from about 0.01 to about 10.

Another significant by-product of the hydroalkylation reaction is cyclohexane. Although a $C_6$-rich stream comprising cyclohexane and unreacted benzene can be readily removed from the hydroalkylation reaction effluent by distillation, owing to the similarity in the boiling points of benzene and cyclohexane, the $C_6$-rich stream is difficult to further separate by simple distillation. However, some or all of the C$_6$-rich stream can be recycled to the hydroalkylation reactor to provide not only part of the benzene feed but also part of the diluents mentioned above.

In some cases, it may be desirable to supply some of the C$_6$-rich stream to a dehydrogenation reaction zone, where the C$_6$-rich stream is contacted with a dehydrogenation catalyst under dehydrogenation conditions sufficient to convert at least part of the cyclohexane in the C$_6$-rich stream portion to benzene, which again can be recycled to the hydroalkylation reaction. The dehydrogenation catalyst generally comprises (a) a support; (b) a hydrogenation-dehydrogenation component; and (c) an inorganic promoter. Conveniently, the support (a) is selected from the group consisting of silica, a silicate, an aluminosilicate, zirconia, and carbon nanotubes, and preferably comprises silica. Suitable hydrogenation-dehydrogenation components (b) comprise at least one metal selected from Groups 6 to 10 of the Periodic Table of Elements, such as platinum, palladium and compounds and mixtures thereof. Typically, the hydrogenation-dehydrogenation component is present in an amount between about 0.1 and about 10 wt % of the catalyst. A suitable inorganic promoter (c) comprises at least one metal or compound thereof selected from Group 1 of the Periodic Table of Elements, such as a potassium compound. Typically, the promoter is present in an amount between about 0.1 and about 5 wt % of the catalyst. Suitable dehydrogenation conditions include a temperature of about 250° C. to about 500° C., a pressure of about atmospheric to about 14.5 psig to 500 psig (100 kPa to 3550 kPa), a weight hourly space velocity of about 0.2 to 50 hr$^{-1}$, and a hydrogen to hydrocarbon feed molar ratio of about 0 to about 20.

Other disadvantageous impurities of the hydroalkylation reaction are bicyclohexyl (BCH) and the methylcyclopentylbenzene (MCPB) isomers which, because of the similarity in their boiling points, are difficult to separate from the desired cyclohexylbenzene by distillation. Moreover, although 1,2-methylcyclopentylbenzene (2-MCPB), and 1,3-methylcyclopentylbenzene(3-MCPB) are readily converted in the subsequent oxidation/cleavage steps to the phenol and methylcyclopentanones, which are valuable products, 1,1-methylcyclopentylbenzene (1-MCPB) is substantially inert to the oxidation step and so, if not removed, will build up in the C$_{12}$ stream. Similarly, bicyclohexyl (BCH) can lead to separation problems downstream. Thus, at least part of the hydroalkylation reaction product may be treated with a catalyst under conditions to remove at least 1,1-methylcyclopentylbenzene, and/or bicyclohexyl from the product. The catalyst is generally an acid catalyst, such as an aluminosilicate zeolite, and especially faujasite and the treatment is conducted at a temperature of about 100° C. to about 350° C., such as about 130° C. to about 250° C., for a time of about 0.1 to about 3 hours, such as about 0.1 to about 1 hours. The catalytic treatment is believed to isomerize the 1,1-methylcyclopentylbenzene to the more readily oxidizable 1,2-methylcyclopentylbenzene (2-MCPB), and 1,3-methylcyclopentylbenzene(3-MCPB). The bicyclohexyl is believed to react with benzene present in the hydroalkylation reaction product to produce cyclohexane and more of the desired cyclohexylbenzene according to the following Reaction-3:

(Reaction-3)

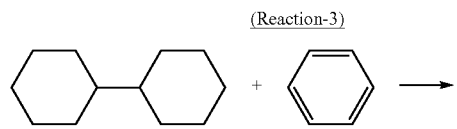

The catalytic treatment can be conducted on the direct product of the hydroalkylation reaction or after distillation of the hydroalkylation reaction product to separate the C$_6$ and/or the heavies fraction.

The cyclohexylbenzene product from the hydroalkylation reaction and any downstream reaction to remove the impurities discussed above is separated from the reaction effluent(s) and is fed to the oxidation reaction described in more detail below.

Oxidation Reaction

In the oxidation step, at least a portion of the cyclohexylbenzene contained in the oxidation feed is converted to cyclohexyl-1-phenyl-1-hydroperoxide, the desired hydroperoxide, according to the following Reaction-4:

(Reaction-4)

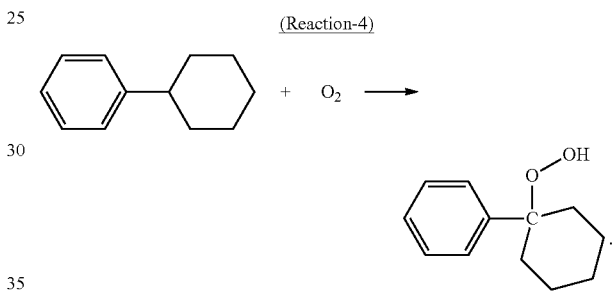

In exemplary processes, the oxidizing step may be accomplished by contacting an oxygen-containing gas, such as air and various derivatives of air, with the feed comprising cyclohexylbenzene. For example, a stream of pure O$_2$, O$_2$ diluted by inert gas such as N$_2$, pure air, or other O$_2$-containing mixtures can be pumped through the cyclohexylbenzene-containing feed in an oxidation reactor.

The oxidation may be conducted in the absence or presence of a catalyst. Examples of suitable oxidation catalysts include those having a structure of formula (FC-I), (FC-II), or (FC-III) below:

(FC-I)

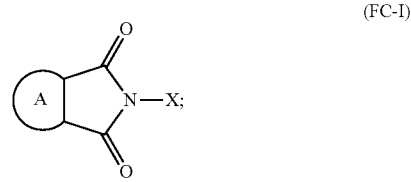

(FC-II)

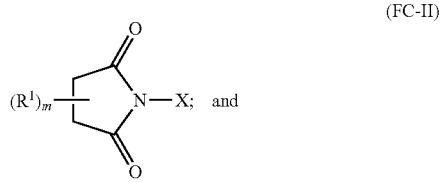

-continued

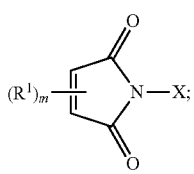
(FC-III)

where:

A represents a ring optionally comprising a nitrogen, sulfur, or oxygen in the ring structure, and optionally substituted by an alkyl, an alkenyl, a halogen, or a N-, S-, or O-containing group or other group;

X represents a hydrogen, an oxygen free radical, a hydroxyl group, or a halogen;

$R^1$, the same or different at each occurrence, independently represents a halogen, a N-, S-, or O-containing group, or a linear or branched acyclic alkyl or cyclic alkyl group having 1 to 20 carbon atoms, optionally substituted by an alkyl, an alkenyl, a halogen, or a N-, S-, or O-containing group or other group; and m is 0, 1 or 2.

Examples of particularly suitable catalysts for the oxidation step include those represented by the following formula (FC-IV):

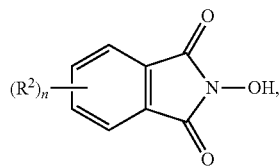
(FC-IV)

where:

$R^2$, the same or different at each occurrence, independently represents a halogen, a N-, S-, or O-containing group, or an optionally substituted linear or branched acyclic alkyl or cyclic alkyl group having 1 to 20 carbon atoms; and n is 0, 1, 2, 3, or 4.

One especially suitable catalyst having the above formula (FC-IV) for the oxidation step is NHPI (N-hydroxyphthalimide). For example, the feed to the oxidizing step can comprise from 10 to 2500 ppm of NHPI by weight of the cyclohexylbenzene in the feed.

Other non-limiting examples of the oxidation catalyst include: 4-amino-N-hydroxyphthalimide, 3-amino-N-hydroxyphthalimide, tetrabromo-N-hydroxyphthalimide, tetrachloro-N-hydroxyphthalimide, N-hydroxyhetimide, N-hydroxyhimimide, N-hydroxytrimellitimide, N-hydroxybenzene-1,2,4-tricarboximide, N,N'-dihydroxy (pyromellitic diimide), N,N'-dihydroxy(benzophenone-3,3', 4,4'-tetracarboxylic diimide), N-hydroxymaleimide, pyridine-2,3-dicarboximide, N-hydroxysuccinimide, N-hydroxy (tartaric imide), N-hydroxy-5-norbornene-2,3-dicarboximide, exo-N-hydroxy-7-oxabicyclo [2.2.1]hept-5-ene-2,3-dicarboximide, N-hydroxy-cis-cyclohexane-1,2-dicarboximide, N-hydroxy-cis-4-cyclohexene-1,2 dicarboximide, N-hydroxynaphthalimide sodium salt, N-hydroxy-o-benzenedisulphonimide, and N,N',N"-trihydroxyisocyanuric acid.

These oxidation catalysts can be used either alone or in conjunction with a free radical initiator, and further can be used as liquid-phase, homogeneous catalysts or can be supported on a solid carrier to provide a heterogeneous catalyst. Desirably, the N-hydroxy substituted cyclic imide or the N,N',N"-trihydroxyisocyanuric acid is employed in an amount from 0.0001 wt % to 15 wt %, such as from 0.001 wt % to 5 wt %, of the cyclohexylbenzene feed.

Non-limiting examples of suitable reaction conditions of the oxidizing step include a temperature in a range from 70° C. to 200° C., such as 90° C. to 130° C., and a pressure in a range from 50 kPa to 10,000 kPa. A basic buffering agent may be added to react with acidic by-products that may form during the oxidation. In addition, an aqueous phase may be introduced into the oxidation reactor. The reaction may take place in a batch or continuous flow fashion.

The reactor used for the oxidizing step may be any type of reactor that allows for the oxidation of cyclohexylbenzene by an oxidizing agent, such as molecular oxygen. A particularly advantageous example of the suitable oxidation reactor is a bubble column reactor capable of containing a volume of the reaction media and bubbling an $O_2$-containing gas stream (such as air) through the media. For example, the oxidation reactor may comprise a simple, largely open vessel with a distributor inlet for the oxygen-containing gas stream. The oxidation reactor may have means to withdraw a portion of the reaction media and pump it through a suitable cooling device and return the cooled portion to the reactor, thereby managing the heat generated in the reaction. Alternatively, cooling coils providing indirect cooling, e.g., by cooling water, may be operated within the oxidation reactor to remove at least a portion of the generated heat. Alternatively, the oxidation reactor may comprise a plurality of reactors in series and/or in parallel, each operating at the same or different conditions selected to enhance the oxidation reaction in the reaction media with different compositions. The oxidation reactor may be operated in a batch, semi-batch, or continuous flow manner well known to those skilled in the art.

Composition of the Oxidation Reaction Product Mixture

Desirably, the oxidation reaction product mixture exiting the oxidation reactor contains cyclohexyl-1-phenyl-1-hydroperoxide at a concentration in a range from Chp1 wt % to Chp2 wt %, based on the total weight of the oxidation reaction product mixture, where Chp1 and Chp2 can be, independently, 5, 10, 15, 20, 25, 30, 35, 40, 45, 50, 55, 60, 65, 70, 75, 80, as long as Chp1<Chp2. Preferably, the concentration of cyclohexyl-1-phenyl-1-hydroperoxide in the oxidation reaction product mixture is at least 20% by weight of the oxidation reaction product mixture. The oxidation reaction product mixture may further comprise residual cyclohexylbenzene at a concentration in a range from Cchb1 wt % to Cchb2 wt %, based on the total weight of the oxidation reaction product mixture, where Cchb1 and Cchb2 can be, independently, 20, 25, 30, 35, 40, 45, 50, 55, 60, 65, 70, 75, 80, 85, 90, 95, as long as Cchb1<Cchb2. Preferably, the concentration of cyclohexylbenzene in the oxidation reaction product mixture is at most 65% by weight of the oxidation reaction product mixture.

In addition, the oxidation reaction product mixture may contain one or more hydroperoxides other than cyclohexyl-1-phenyl-1-hydroperoxide generated as byproduct(s) of the oxidation reaction of cyclohexylbenzene, or as the oxidation reaction product of oxidizable component(s) other than cyclohexylbenzene that may have been contained in the feed supplied to the oxidizing step, such as cyclohexyl-2-phenyl-1-hydroperoxide, cyclohexyl-3-phenyl-1-hydroperoxide, and methylcyclopentylbenzene hydroperoxides. These undesired hydroperoxides are present at a total concentration from Cu1 wt % to Cu2 wt %, where Cu1 and Cu2 can be, independently, 0.1, 0.2, 0.3, 0.5, 0.7, 0.9, 1.0, 1.2, 1.4, 1.5, 1.6, 1.8, 2.0, 2.5, 3.0, 3.5, 4.0, 4.5, 5.0, 6.0, 7.0, 8.0, as long as Cu1<Cu2. They are undesirable because they may not convert into phenol and cyclohexanone in the cleavage reaction at the desired conversion and/or selectivity, resulting in overall yield loss.

As noted above, the oxidation reaction product mixture may also contain phenol as a further by-product of the oxidation reaction. The concentration of phenol (CPh) in the oxidation reaction product mixture exiting the oxidation reactor(s) can range from CPh1 ppm to CPh2 ppm, where CPh1 and CPh2 can be, independently: 50, 60, 70, 80, 90, 100, 150, 200, 250, 300, 350, 400, 450, 500, 550, 600, 650, 700, 750, 800, 850, 900, 950, 1000, 1500, 2000, as long as CPh1<CPh2.

The oxidation reaction product mixture may contain water. The concentration of water in the oxidation reaction product mixture exiting the oxidation reactor may range from C1a ppm to C1b ppm, based on the total weight of the oxidation reaction product mixture, where C1a and C1b can be, independently: 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, 3000, 3500, 4000, 4500, or 5000, as long as C1a<C1b.

The oxidation reaction product mixture may also contain part or all of any catalyst, such as NHPI, supplied to the oxidizing step. For example, the oxidation reaction product mixture may contain from 10 to 2500 ppm of NHPI, such as from 100 to 1500 ppm by weight of NHPI.

Treatment of the Oxidation Reaction Product Mixture

In the process of the present disclosure, before being supplied to the cleavage step, at least a portion of the oxidation reaction product mixture may be separated. The separation process may include subjecting at least a portion of the oxidation reaction product mixture to vacuum evaporation so as to recover: (i) a first fraction comprising the majority of the cyclohexyl-1-phenyl-1-hydroperoxide and other higher boiling components of the oxidation reaction product mixture portion, such as other hydroperoxides and NHPI catalyst, if present in the oxidation reaction product mixture portion; and (ii) a second fraction comprising a major portion of the cyclohexylbenzene, phenol, if any, and other lower boiling components of the oxidation reaction product mixture portion.

Desirably, in the first fraction, the concentration of cyclohexyl-1-phenyl-1-hydroperoxide can range from Cc1 wt % to Cc2 wt %, and the concentration of cyclohexylbenzene can range from Cd1 wt % to Cd2 wt %, based on the total weight of the first fraction, where Cc1 and Cc2 can be, independently, 40, 45, 50, 55, 60, 65, 70, 75, 80, 85, 90, as long as Cc1<Cc2; and Cd1 and Cd2 can be, independently, 10, 15, 20, 25, 30, 35, 40, 45, 50, as long as Cd1<Cd2.

Advantageously, in the second fraction, the concentration of cyclohexyl-1-phenyl-1-hydroperoxide can range from Cc3 wt % to Cc4 wt %, and the concentration of cyclohexylbenzene can range from Cd3 wt % to Cd4 wt %, based on the total weight of the second fraction, where Cc3 and Cc4 can be, independently, 0.01, 0.05, 0.10, 0.20, 0.40, 0.50, 0.60, 0.80, 1.00, 1.50, 2.00, 2.50, 3.00, 3.50, 4.00, 4.50, 5.00, as long as Cc3<Cc4; and Cd3 and Cd4 can be, independently, 90, 92, 94, 95, 96, 97, 98, or even 99, as long as Cd3<Cd4.

Because cyclohexylbenzene hydroperoxide is prone to decomposition at elevated temperatures, e.g., at above 150° C., the vacuum evaporation step to separate the oxidation reaction product mixture into the first and second fractions is conducted at a relatively low temperature, e.g., no higher than 130° C., or no higher than 120° C., or even no higher than 110° C. Cyclohexylbenzene has a high boiling point (239° C. at 101 kPa). Thus, at acceptable cyclohexylbenzene-removal temperatures, cyclohexylbenzene tends to have very low vapor pressure. Accordingly, preferably, to effectively remove a meaningful amount of cyclohexylbenzene from the oxidation reaction product mixture, the oxidation reaction product mixture is subjected to a very low absolute pressure, e.g., in a range from Pc1 kPa to Pc2 kPa, where Pc1 and Pc2 can be, independently, 0.05, 0.10, 0.15, 0.20, 0.25, 0.26, 0.30, 0.35, 0.40, 0.45, 0.50, 0.60, 0.65, 0.70, 0.75, 0.80, 0.85, 0.90, 0.95, 1.00, 1.50, 2.00, 2.50, 3.00, as long as Pc1<Pc2. Particularly advantageously, Pc1=0.25, and Pc2=1.5.

After separation of the oxidation reaction product mixture into the first and second fractions, part or all of the first fraction can be routed directly to the cleavage step. All or a portion of the first fraction may be cooled before passage to the cleavage step so as to cause crystallization of the unreacted imide oxidation catalyst. The imide crystals may then be recovered for reuse either by filtration or by scraping from a heat exchanger surface used to effect the crystallization.

The second fraction produced from the oxidation reaction product mixture may be treated to reduce the level of phenol therein before part or all of the cyclohexylbenzene in the second fraction is recycled to the hydrogenation.

Treatment of the second fraction can comprise contacting at least a portion of the second fraction with an aqueous composition comprising a base under conditions such that the base reacts with the phenol to produce a phenoate species which remains in the aqueous composition. A strong base, that is a base having a $pK_b$ value less than 3, such as less than 2, 1, 0, or −1, is desirably employed in the treatment of the second fraction. Particularly suitable bases include hydroxides of alkali metals (e.g., LiOH, NaOH, KOH, RbOH), hydroxides of alkaline earth metals ($Mg(OH)_2$, $Ca(OH)_2$, $Sr(OH)_2$, $Ba(OH)_2$), and mixtures of one or more thereof. Phenol can react with these hydroxides to form phenoates, which typically have higher solubility in water than phenol per se. A particularly desirable base is NaOH, which is cost efficient and capable of reacting with phenol in the second fraction to produce sodium phenoate. It should be noted that, when a hydroxide is used as the base, because of the reaction of $CO_2$ present in the atmosphere with the hydroxide, the aqueous composition may comprise, at various concentrations, one or more of a corresponding carbonate, bicarbonate, or carbonate-hydroxide complex. Desirably, the aqueous composition comprising the base has a pH of at least 8, preferably at least 10.

Contacting of the second fraction with the aqueous composition comprising a base produces an aqueous phase containing at least part of the phenol and/or a derivative thereof from the second fraction and an organic phase containing cyclohexylbenzene and having a reduced concentration of phenol as compared with the second fraction. Desirably, the phenol concentration in the organic phase is in the range from CPh7 ppm to CPh8 ppm, based on the total weight of the organic phase, where CPh7 and CPh8 can be, independently: 0, 10, 20, 30, 40, 50, 100, 150, 200, 250, as long as CPh7<CPh8.

The organic phase can then be separated from the aqueous phase, for example, spontaneously under gravity, and can then be recycled to the oxidizing step as a third fraction either directly, or more preferably, after water washing to remove base entrained in the organic phase.

Cleavage Reaction

In the cleavage reaction, at least a portion of the cyclohexyl-1-phenyl-1-hydroperoxide decomposes in the presence of an acid catalyst in high selectivity to cyclohexanone and phenol according to the following desired Reaction-5:

(Reaction-5)

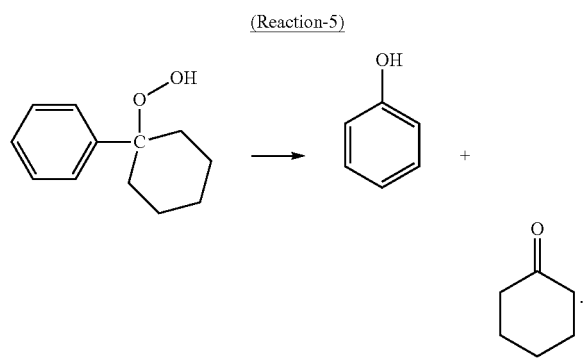

The cleavage product mixture may comprise the acid catalyst, phenol, cyclohexanone, cyclohexylbenzene, and contaminants.

The acid catalyst used in the present cleavage reaction comprises a solid acid catalyst, such an acidic molecular sieve, for example an aluminosilicate zeolite. Examples of suitable acidic molecular sieves include at least one of zeolite beta, faujasite, ZSM-12, mordenite and an MCM-22 family molecular sieve. The cleavage catalyst may comprise a FAU-type zeolite having a unit cell size less than 24.50 Angstroms ("Å"), such as less than or equal to 24.45 Å, or less than or equal to 24.40 Å, or less than or equal to 24.35 Å, or less than or equal to 24.30 Å, or even less than or equal to 24.25 Å. Unit cell size is determined by X-ray diffraction as described in ASTM D-3942. As used herein, the terms "faujasite," "FAU-type zeolite" and "zeolite of the FAU type" are used interchangeably to mean a zeolite having a FAU-type structure as described in the *Atlas of Zeolite Framework Types*, Ch. Baerlocher et al. (6th Ed. 2007). The zeolite can be used in unbound form or can be combined with a binder, such as silica or alumina, such that the overall catalyst (zeolite plus binder) comprises from about 5 wt % to about 95 wt % of the final catalyst material.

The cleavage catalyst may have a pore volume as measured by nitrogen ($N_2$) adsorption of at least 0.3 cm$^3$/g, or at least 0.4 cm$^3$/g, or at least 0.5 cm$^3$/g. The cleavage catalyst may comprise at most 6 wt %, or at most 3 wt %, or at most 1 wt %, or at most 0.5 wt % of Group 3 to Group 12 metals including the lanthanide series, based upon the weight of the catalyst.

Preferably, the cleavage reaction is conducted under conditions including: (i) a temperature in a range from T1° C. to T2° C., where T1 and T2 can be, independently, 20, 30, 40, 50, 60, 70, 80, 90, 100, 110, 120, 130, 140, 150, 160, 170, 180, 190, or 200, as long as T1<T2; (ii) an absolute pressure in a range from P1 kPa to P2 kPa, where P1 and P2 can be, independently, 100, 200, 300, 400, 500, 600, 700, 800, 900, 1000, 1100, 1200, 1300, 1400, 1500, 1600, 1700, 1800, 1900, 2000, as long as P1<P2, such that the cleavage reaction mixture is completely or predominantly in the liquid phase during the cleavage reaction; and (iii) a weight hourly space velocity in a range from WHSV1 hour$^{-1}$ to WHSV2 hour$^{-1}$, where WHSV1 and WHSV2 can be, independently, 1, 2, 3, 4, 5, 6, 7, 8, 9, 10, 20, 30, 40, 50, 60, 70, 80, 90, 100, 200, 300, 400, 500, 600, 700, 800, 900, or 1000, as long as WHSV1<WHSV2.

The cleavage reaction can be conducted in a variety of reactor configurations and in either a single reactor or in a plurality of reactors. For example, the reaction may be conducted at least in a first reactor and a second reactor connected in series, with the first reactor being operated at a temperature of about 20° C. to about 120° C. and an absolute pressure of about 100 kPa to about 500 kPa and the second reactor being operated at a temperature of about 40° C. to about 180° C. and an absolute pressure of about 100 kPa to about 1000 kPa. The first and second reactors may be the same or different and may also be connected in parallel such that neither receive as its feed an effluent from the other reactor.

The cleavage reaction may be conducted in a slurry reactor, in a configuration such as a stirred tank, pump-around loop. At least part of the cleavage reaction can be conducted in a continuous stirred tank reactor (CSTR), with the catalyst being slurried in the cleavage reaction medium. The catalyst can be used in an amount from 50 ppm to 20,000 ppm by weight of the cleavage reaction medium. Advantages for this configuration include easy heat management and flexibility to add/withdraw catalyst to maintain conversion as the catalyst deactivates over time. If peroxide cleavage is performed with the oxidation product containing the imide catalyst used in the oxidation step, the latter may also adsorb on the catalyst, inhibiting the performance of the solid acid catalyst. Thus, the imide catalyst adsorbed on the catalyst can be removed or recovered by recovering the imide-loaded catalyst from the cleavage reactor and washing this spent catalyst with a polar solvent such as acetone or cyclohexanone to recover its cleavage activity and imide adsorbing capacity (rejuvenation of the catalyst). The deactivated catalyst can be also regenerated by burning off coke in air. In case the catalyst is also used for recovery of the imide catalyst, this air-regeneration is advantageously performed after recovering the adsorbed catalyst by washing using a solvent. In a slurry cleavage process, the catalyst can be regenerated on various schedules. Advantageously, the catalyst can be continuously withdrawn from the cleavage reactor, regenerated in an external recycle loop, and then returned into the cleavage reactor. Under such an operation regime, a steady state of catalyst activity can be maintained through regeneration and by continuously replacing a fraction of the recycled catalyst with fresh catalyst.

The solid acid catalyst can also be used in a fixed bed plug-flow reactor with or without first removing the imide catalyst from the cleavage feed stream. If the imide catalyst is not removed, the catalyst bed will adsorb it, allowing its recovery and recycle to the oxidation process. In such a process design, two or more parallel cleavage reactor trains may be employed to enable uninterrupted processing of the peroxide feed. Thus, as the catalyst is saturated with the imide catalyst causing it to deactivate in one reactor train, the cleavage feed can be switched to another reactor train that contains fresh or regenerated catalyst. The imide-saturated catalyst can be rejuvenated off-line by, for example, flushing with a polar solvent such as acetone or cyclohexanone. The imide catalyst recovered can be re-used for oxidation. The coke on catalyst can then also be removed by burning in air before the regenerated reactor train is returned to cleavage operation to replace the previously operating reactor train that can now be taken off-line for regeneration. This cycle then can be repeated until the catalyst in one or more reactor trains can no longer be regenerated to acceptable levels. In such cases, the exhausted catalyst can simply be replaced with a fresh charge before returning the train to cleavage operations.

The cleavage reaction using the solid acid catalyst may have a cyclohexylbenzene hydroperoxide conversion in a range from Cp1% to Cp2%, where Cp1 and Cp2 can be, independently, 30, 40, 50, 60, 70, 80, 90, 91, 92, 93, 94, 95, 96, 97, 98, 99, or 100, as long as Cp1<Cp2. The phenol selectivity may be in a range from Sp1% to Sp2%, where Sp1 and Sp2 can be, independently, 50, 55, 65, 70, 75, 80, 85, 90, 91, 92, 93, 94, 95, 96, 97, 98, 99, or 100, as long as Sph1<Sph2. The cyclohexanone selectivity may be in a range from Sc1% to Sc2%, where Sc1 and Sc2 can be, independently, 50, 55, 65, 70, 75, 80, 85, 90, 91, 92, 93, 94, 95, 96, 97, 98, 99, or 100, as long as Sc1<Sc2. As used herein, "cyclohexylbenzene hydroperoxide conversion" means the percentage of cyclohexylbenzene hydroperoxide converted to any product, including but not limited to phenol and cyclohexanone. Phenol selectivity (Sp) and cyclohexanone selectivity (Sc) are calculated as follows:

$$Sp = \frac{\text{Amount of phenol produced (mole)}}{\text{Amount of cyclohexylbenzene hydroperoxide converted (mole)}} \times 100\%$$

$$Sc = \frac{\text{Amount of cyclohexanone produced (mole)}}{\text{Amount of cyclohexylbenzene hydroperoxide converted (mole)}} \times 100\%$$

The major products of the cleavage reaction are phenol and cyclohexanone, each of which generally constitutes from C1 wt % to C2 wt % of the cleavage effluent, based on the weight of the conversion products of the cleavage reaction, where C1 and C2 can be, independently, 40, 41, 42, 43, 44, 45, 46, 47, 48, 49, 50, 51, 52, 53, 54, 55, 56, 57, 58, 59, 60, as long as C1<C2, and the total amount of phenol and cyclohexanone are no more than 100% of the cleavage effluent.

The cleavage effluent is removed from the cleavage reaction zone and is divided into at least a cleavage product stream, from which phenol and/or cyclohexanone can be recovered, and a cleavage recycle stream, which is returned to the cleavage reaction zone to form part of a cleavage reaction mixture with the cyclohexylbenzene hydroperoxide from the oxidation step. The recycle stream is used to control exothermic heat rise in the cleavage reaction zone and, the weight ratio of the cleavage recycle stream to the cleavage product stream may range from R1 to R2, where R1 and R2 can be, independently, 1, 2, 3, 4, 5, 6, 7, 8, 9, 10, 15, 20, 25, 30, 35, 40, 45, 50. Division of the cleavage effluent into at least the cleavage product stream and the cleavage recycle stream may or may not involve a fractionation step to reduce the level of one or more of components in the recycle stream (such as, phenol, cyclohexanone and/or cyclohexylbenzene) as compared with the cleavage effluent.

In the present process a polar solvent is also supplied to the cleavage reaction zone along with the cyclohexylbenzene hydroperoxide from the oxidation step and the cleavage recycle stream. The polar solvent may be added to the cleavage reaction zone as a separate stream, together with the cyclohexylbenzene hydroperoxide-containing stream from the oxidation step as a combined stream or, most desirably, together with the cleavage recycle stream in a combined stream. This is because, due to the high phenol concentration in the recycle stream, the recycle stream tends to have a higher polarity than the fresh cyclohexylbenzene hydroperoxide stream and would mix better with the polar solvent. Suitable polar solvents include alcohols containing less than 6 carbons, such as ethanol, methanol, phenol, propanol, isopropanol and butanols. However, many of these organic solvents may react with cyclohexanone and thus influence product yield and purity under the cleavage reaction conditions. Thus, the preferred polar solvent is water. Although the mechanism is not fully understood, the polar solvent is found to decrease the deactivation rate of the solid acid catalyst used in the cleavage reaction.

The polar solvent can be added to the cleavage reaction zone in an amount from C1 wt % to C2 wt %, based on the total weight of the cleavage reaction mixture, where C1 and C2 can be, independently, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, as long as C1<C2. The cleavage reaction mixture may contain from Cp1 wt % to Cp2 wt % of phenol, Cchn1 wt % to Cchn2 wt % of cyclohexanone, Cchp1 wt % to Cchp2 wt % of cyclohexylbenzene hydroperoxide, and Cchb1 wt % to Cchb2 wt % of cyclohexylbenzene, based on the total weight of the cleavage reaction mixture, where Cp1, Cp2, Cchn1, and Cchn2 can be, independently, 5, 6, 7, 8, 9, 10, 15, 20, 25, 30, 35, 40, 45, 50, 55, 60, 65, 70, as long as Cp1<Cp2, and Cchn1<Cchn2; Cchp1 and Cchp2 can be, independently, 0.1, 0.2, 0.4, 0.5, 0.6, 0.8, 1, 2, 3, 4, 5, 6, 7, 8, 9, 10, as long as Cchp1<Cchp2; and Cchb1 and Cchb2 can be, independently, 1, 2, 3, 4, 5, 6, 7, 8, 9, 10, 15, 20, 25, 30, 35, 40, 45, 50, 55, 60, as long as Cchb1<Cchb2. Preferably, the cleavage reaction mixture contains from 20 wt % to 40 wt % phenol, from 20 wt % to 40 wt % cyclohexanone, no greater than 6 wt % cyclohexylbenzene hydroperoxide, and from 15 wt % to 40 wt % cyclohexylbenzene.

Separation and Purification

As discussed above, the cleavage product mixture may comprise one or more contaminants. The processes may further comprise contacting at least a portion of a contaminant with an acidic material to convert at least a portion of the contaminant to a converted contaminant, thereby producing a modified product mixture. Detailed description of the contaminant treatment process can be found, e.g., in International Publication WO2012/036822A1, the relevant content of which is incorporated herein by reference in its entirety.

At least a portion of the cleavage product mixture may be subjected to a neutralization reaction. Where a liquid acid such as sulfuric acid is used as the cleavage catalyst, it is highly desirable that the cleavage reaction product mixture is neutralized by a base, such as an organic amine (e.g., methylamine, ethylamine, diamines such as methylenediamine, propylene diamine, butylene diamine, pentylene diamine, hexylene diamine, and the like) before the mixture is subjected to separation to prevent equipment corrosion by the acid. Desirably, the thus formed amine sulfate salt has a boiling point higher than that of cyclohexylbenzene.

The neutralized cleavage reaction product mixture can then be separated by methods such as distillation. In one example, in a first fractionation column after the cleavage reactor, a heavies fraction comprising the amine salt is obtained at the bottom of the column, a side fraction comprising cyclohexylbenzene is obtained in the middle section, and an upper fraction comprising cyclohexanone, phenol, methylcyclopentanone, and water is obtained.

The separated cyclohexylbenzene fraction can then be treated and/or purified before being delivered to the oxidizing step. Since the cyclohexylbenzene separated from the cleavage product mixture may contain phenol and/or olefins such as cyclohexenylbenzenes, the material may be subjected to treatment with an aqueous composition comprising a base as described above for the second fraction of the oxidation product mixture and/or a hydrogenation step as disclosed in, for example, WO2011/100013A1, the entire contents of which are incorporated herein by reference.

In one example, the fraction comprising phenol, cyclohexanone, and water can be further separated by simple distillation to obtain an upper fraction comprising primarily cyclohexanone and methylcyclopentanone and a lower stream comprising primarily phenol, and some cyclohexanone. Cyclohexanone cannot be completely separated form phenol without using an extractive solvent due to an azeotrope formed between these two. Thus, the upper fraction can be further distillated in a separate column to obtain a pure cyclohexanone product in the vicinity of the bottom and an impurity fraction in the vicinity of the top comprising primarily methylcyclopentanone, which can be further purified, if needed, and then used as a useful industrial material. The lower fraction can be further separated by a step of extractive distillation using an extractive solvent (e.g., glycols such as ethylene glycol, propylene glycol, diethylene glycol, triethylene glycol, and the like) described in, e.g., co-assigned, co-pending patent applications WO2013/165656A1 and WO2013/165659, the contents of which are incorporated herein by reference in their entirety. An upper fraction comprising cyclohexanone and a lower fraction comprising phenol and the extractive solvent can be obtained. In a subsequent fractionation column, the lower fraction can then be separated to obtain an upper fraction comprising a phenol product and a lower fraction comprising the extractive solvent.

Uses of Cyclohexanone and Phenol

The cyclohexanone produced through the processes disclosed herein may be used, for example, as an industrial solvent, as an activator in oxidation reactions and in the production of adipic acid, cyclohexanone resins, cyclohexanone oxime, caprolactam, and nylons, such as nylon-6 and nylon-6,6. The phenol produced through the processes disclosed herein may be used, for example, to produce phenolic resins, bisphenol A, ε-caprolactam, adipic acid, and/or plasticizers.

EXAMPLES

In a series of three tests, a fresh fixed bed of faujasite catalyst was used in a cleavage reactor with the ability to recycle the product.

Test A, in Recycle Mode

In this test, an oxidation product mixture comprising 20-25% of cyclohexylbenzene hydroperoxide and the balance primarily cyclohexylbenzene was fed to the cleavage reactor at a WHSV of about 5 hour$^{-1}$ with a product recycle to feed ratio set in the range from 10:1 to 20:1. The catalyst activity is then monitored by calculating the reaction rate observed at different times.

Test B, in Simulated Recycle Mode

In this test, an oxidation product mixture comprising 20-25% of cyclohexylbenzene hydroperoxide and the balance primarily cyclohexylbenzene was diluted with equal amounts of phenol and cyclohexanone. The resultant material was then fed to the cleavage reactor identical with the one used in Test A on a once-through basis, i.e. with no recycle of the products, so as to simulate the feed the catalyst would be exposed to if the reactor were operating with the oxidation product mixture as feed and a 5:1 product/feed recycle ratio (i.e., a feed comprising about 5% cyclohexylbenzene hydroperoxide, about 10% phenol, about 10% cyclohexanone, and balance cyclohexylbenzene).

Test C, in Simulated Recycle Mode with Added Water

In this test, an oxidation product mixture comprising 20-25% of cyclohexylbenzene hydroperoxide and the balance primarily cyclohexylbenzene was diluted with equal amounts of phenol and cyclohexanone. The resultant material was then treated with water such that it becomes saturated with water, and subsequently fed to the reactor identical with the one used in Test A on a once-through basis, i.e., with no recycle of the products, so as to simulate the feed the catalyst would see if the reactor were operating with oxidation product as feed and a 5:1 product to feed ratio recycle (i.e., a feed comprising about 5% cyclohexylbenzene hydroperoxide, about 10% phenol, about 10% cyclohexanone, and balance cyclohexylbenzene, which is saturated with water).

The calculated rates in each experiment were then normalized with respect to the initial rate in that experiment and plotted as a function of the amount of cyclohexylbenzene hydroperoxide converted per gram of catalyst, shown in FIG. 1. Data points 101 correspond to Test A, data points 103 to Test B, and data points 105 to Test C. As this diagram clearly shows, in Test C, when water is added to the feed, the life of the catalyst was much longer than in Tests A and B, where no water was intentionally added into the feed.

The contents of all reference cited herein are incorporated in their entities by reference thereto.

While the present invention has been described and illustrated by reference to particular embodiments, those of ordinary skill in the art will appreciate that the invention lends itself to variations not necessarily illustrated herein. For this reason then, reference should be made solely to the appended claims for purposes of determining the true scope of the present invention.

The invention claimed is:

1. A continuous process for producing phenol, the process comprising:
    (a) continuously supplying a cleavage feed comprising cyclohexylbenzene hydroperoxide to a cleavage reaction zone;
    (b) continuously contacting a cleavage reaction mixture comprising the cleavage feed in the cleavage reaction zone with a solid acid catalyst under conditions effective to continuously produce a cleavage effluent comprising phenol and cyclohexanone, wherein the cleavage reaction mixture further comprises from 20 wt % to 40 wt % phenol;
    (c) dividing the cleavage effluent into at least a cleavage product and a cleavage recycle; and
    (d) supplying the cleavage recycle and a polar solvent to the cleavage reaction zone to produce the cleavage reaction mixture with the cleavage feed;
    wherein at least part of the polar solvent is combined with the cleavage recycle to produce a combined stream which is continuously supplied to the cleavage reaction zone in (d).

2. The process of claim 1, wherein the polar solvent is supplied to the cleavage reaction zone in (d) in an amount from 100 ppm to 10% by weight of the cleavage reaction mixture.

3. The process of claim 2, wherein the polar solvent is supplied to the cleavage reaction zone in (d) in an amount from 1000 ppm to 5% by weight of the cleavage reaction mixture.

4. The process of claim 1, wherein the polar solvent is water.

5. The process of claim 1, wherein the cleavage effluent comprises unreacted cyclohexylbenzene hydroperoxide.

6. The process of claim 1, wherein the solid acid catalyst comprises an acidic molecular sieve.

7. The process of claim 6, wherein the acidic molecular sieve comprises an aluminosilicate zeolite.

8. The process of claim 6, wherein the acidic molecular sieve comprises at least one of zeolite beta, faujasite, ZSM-12, mordenite and an MCM-22 family molecular sieve.

9. The process of claim 6, wherein the acidic molecular sieve comprises faujasite.

10. The process of claim 6, wherein the acidic molecular sieve comprises faujasite having a unit cell size of less than 24.50 Å.

11. The process of claim 1, wherein the conditions in (b) include a temperature from about 20° C. to about 200° C. and an absolute pressure from about 100 kPa to about 2000 kPa.

12. A continuous process for producing phenol, the process comprising:
   (a) hydroalkylating benzene with hydrogen in the presence of a hydroalkylation catalyst under conditions effective to produce a hydroalkylation reaction product comprising cyclohexylbenzene;
   (b) contacting at least a portion of the cyclohexylbenzene from the hydroalkylation reaction product with oxygen in the presence of an oxidation catalyst under oxidation conditions effective to produce an oxidation product comprising cyclohexylbenzene hydroperoxide;
   (c) supplying at least a portion of the oxidation product comprising cyclohexylbenzene hydroperoxide to a cleavage reaction zone;
   (d) continuously contacting a cleavage reaction mixture comprising the said oxidation product portion in the cleavage reaction zone with a solid acid catalyst under conditions effective to continuously produce a cleavage effluent comprising phenol and cyclohexanone, wherein the cleavage reaction mixture further comprises from 20 wt % to 40 wt % phenol;
   (e) dividing the cleavage effluent into at least a cleavage product and a cleavage recycle; and
   (f) supplying the cleavage recycle and a polar solvent to the cleavage reaction zone to produce the cleavage reaction mixture with said oxidation product portion;
   wherein at least part of the polar solvent is combined with the cleavage recycle to produce a combined stream which is continuously supplied to the cleavage reaction zone in (f).

13. The process of claim 12, wherein the polar solvent is supplied to the cleavage reaction zone in (f) in an amount such that the cleavage reaction mixture comprises from 100 ppm to 10% by weight of the polar solvent.

14. The process of claim 12, wherein the polar solvent is supplied to the cleavage reaction zone in (f) in an amount such that the cleavage reaction mixture comprises from 1000 ppm to 5% by weight of the polar solvent.

15. The process of claim 12, wherein the polar solvent is water.

16. The process of claim 12, wherein the cleavage effluent comprises unreacted cyclohexylbenzene hydroperoxide.

17. The process of claim 12, wherein the solid acid catalyst comprises an acidic molecular sieve.

18. The process of claim 17, wherein the acidic molecular sieve comprises an aluminosilicate zeolite.

19. The process of claim 17, wherein the acidic molecular sieve comprises at least one of zeolite beta, faujasite, ZSM-12, mordenite and an MCM-22 family molecular sieve.

20. The process of claim 17, wherein the acidic molecular sieve comprises faujasite.

21. The process of claim 17, wherein the acidic molecular sieve comprises faujasite having a unit cell size of less than 24.50 Å.

22. The process of claim 12, wherein the conditions in (b) include a temperature from about 20° C. to about 200° C. and a pressure from about 100 kPa to about 2000 kPa.

* * * * *